United States Patent [19]

Davidson et al.

[11] Patent Number: 5,344,494

[45] Date of Patent: Sep. 6, 1994

[54] METHOD FOR CLEANING POROUS AND ROUGHENED SURFACES ON MEDICAL IMPLANTS

[75] Inventors: James A. Davidson, Germantown; Ajit K. Mishra, Memphis, both of Tenn.

[73] Assignee: Smith & Nephew Richards, Inc., Memphis, Tenn.

[21] Appl. No.: 7,338

[22] Filed: Jan. 21, 1993

[51] Int. Cl.$^5$ .......................... B08B 7/00; B08B 3/12
[52] U.S. Cl. ............................................. 134/7; 134/1; 134/42; 51/307; 451/39
[58] Field of Search ................. 134/7, 42, 1; 51/307, 51/320

[56] References Cited

U.S. PATENT DOCUMENTS

| | | | |
|---|---|---|---|
| 5,057,108 | 10/1991 | Shetty et al. | 606/53 |
| 5,095,925 | 3/1992 | Elledge et al. | 134/61 |
| 5,160,547 | 11/1992 | Kirschner et al. | 134/7 |
| 5,211,663 | 5/1993 | Kovacs et al. | 623/16 |

FOREIGN PATENT DOCUMENTS

| | | |
|---|---|---|
| 3720992A1 | 1/1989 | Fed. Rep. of Germany . |
| 133914 | 10/1979 | German Democratic Rep. . |
| 62-137848 | 12/1988 | Japan . |
| 4079326 | 3/1992 | Japan . |
| 1397102 | 11/1975 | United Kingdom . |

*Primary Examiner*—Richard Dean
*Assistant Examiner*—Zeinab El-Arini
*Attorney, Agent, or Firm*—Pravel, Hewitt, Kimball & Krieger

[57] ABSTRACT

A method for the cleaning of roughened surface or porous-coated medical implants of all kinds. In the cleaning method, the roughened surface or porous-coated implant is subjected to blasting with particulate solids selected from the solids that are soluble in a biocompatible non-toxic solvent and solids that deliquesce, sublimate or vaporize. The particulate solids must be sufficiently hard to provide effective impact for dislodging debris and loosely attached particles from implant surfaces. After blasting, the surface is optionally treated with ultrasonic vibration to further remove debris particulates. The impacted surfaces may also be rinsed with a biocompatible liquid. After cleaning, the surfaces may be passivated by immersion in conventional passivation solutions or a solution of non-aggressive oxyanions.

15 Claims, 1 Drawing Sheet

METHOD FOR CLEANING POROUS AND ROUGHENED SURFACES ON MEDICAL IMPLANTS

BACKGROUND OF THE INVENTION

1. Field of the Invention

The invention relates to a method for cleaning the surfaces of medical implants. More specifically, the invention provides a method for cleaning medical implants provided with a porous coating to reduce debris particulates in the coating and remove loosely adherent coating particles, thereby providing a more biocompatible medical implant.

2. Description of the Related Art

It is often desirable to provide medical implants with a roughened (i.e. grit-blasted, peened, etc.) surface or porous coating that will promote bone and tissue integration or ingrowth into surface pores thereby enhancing the fixation of the medical implant in a recipient's body. A porous coating may consist of sintered beads, diffusion bonded wire-mesh, plasma-sprayed metallic powders and the like. These roughened surfaces or porous coatings may advantageously be applied to the surfaces of a variety of medical implants such as orthopedic implants, dental implants, cardiovascular implants, and the like, to obtain the advantages of tissue ingrowth, tissue coating, cell attachment, or to promote bone ingrowth and superior fixation of the implant in the recipient's skeletal structure.

The conventional techniques for fabricating porous coatings on medical implants often produce two undesirable effects: small sections of the porous coatings are loosely adherent and coating particulates may become dislodged after implantation in the recipient's body; and loosely-held debris, produced in the coating process and remaining on the porous coating surface, separate from the surface and enter the recipient's body tissue after implantation of the implant. Similarly, loose or near-loose surface contaminants or metal particles may exist on grit-blasted, peened, or other types of roughened surfaces with similar consequences. The release of these debris and loosely adherent coating particulates into the body are cause for serious concern. Particulate debris produced by orthopedic implants can cause cell lysis and, in the case of for instance a hip stem prosthesis, stem abrasion, bone resorption and loosening of the implant. Further, detached debris may migrate into the spaces between articulating surfaces of a prosthetic joint and cause excessive wear of the joint thereby increasing the rate of generation of debris and aggravating adverse cell tissue responses, while reducing the useful life of the implant.

In order to minimize the amount of debris that a porous coated medical implant will release, conventional cleaning methods are currently employed. These include blasting the surface of the porous coated implant with particles of a hard material such as alumina, silicon carbide, steel shot, glass beads and the like, to remove loosely adherent coating particles and to dislodge other manufacturing debris. However, these cleaning methods produce "cross contamination" in that fragments of the hard particles used in the shot blasting cleaning process also adhere to the porous coated surfaces, which are by their very nature not smooth but which contain numerous tiny interstices into which fine particles may lodge. After implantation, the action of the recipient's body fluids and tissue and mechanical stresses exerted on the implant result in the release of this cross contamination debris into the body potentially leading to medically harmful effects.

What is needed is a method for cleaning medical implants which have undergone various surface roughening processes or that are coated with a porous coating that will not damage the coating, that will not cross contaminate the coating, and that will remove substantially all the manufacturing debris and any loosely adherent porous coating particles from the implant's surface.

U.S. Pat. No. 5,057,108 relates to a surface treatment process for stainless steel orthopedic implant devices. In this process, the stainless steel orthopedic implants are first blasted with stainless steel shot. This cold works the surface by introducing residual compressive stresses in the surface. This steel shot blasting treatment is followed by blasting with smaller sized glass beads, which is represented as improving the fatigue properties of the surface by working those areas not covered by the larger steel shot. Further, it is alleged that glass bead blasting helps clean the surface of any residual steel shot that may have been transferred to the target surface. After these two blasting steps, the surface is electropolished and then passivated by immersion in nitric acid solution to produce a protective oxide film on the finished part. Significantly, the patent does not address medical implants coated with a porous coating. Such a coating would become contaminated with fragments of stainless steel and glass bead shot. The subsequent electro-polishing and passivation treatments would not remove this cross contamination debris.

Likewise, East German patent application 133 914 relates to a process for cleaning continuous metal plate surfaces with a two-component medium. The medium includes (1) a carrier which can be gaseous carbon dioxide, sodium hydroxide solution, or other chemically active solutions; and (2) a granular solid selected from hard particles such as silicon carbide, glass beads, and the like. While the process uses granular solid hard particles which are hard enough that they do not stick to the surface being cleaned and thus do not leave large amounts of residue, these particles are not soluble in liquids used for cleaning and, thus, must leave microscopic residual particles on the surface being cleaned. This would be undesirable in medical implants since small particulate debris is the most potent initiator of adverse cell response. Furthermore, the patent application does not address the problems encountered in cleaning a roughened surface or porous-coated medical implant of surface debris and loosely held coating particulates.

Japan Laid Open 137 848 is directed to the "polishing" of surfaces with ice particles. It is represented that ice particles, due to their low density, will present a relatively low impact when blasted onto a metal surface for polishing and are therefore not very effective as a polishing medium. It is asserted that acid or alkali frozen solutions should be used as shot particles to achieve mechanical polishing, etching and degreasing of a surface at the same time. The treatment of porous-coated medical implants to remove surface debris or loosely held coating particulates is not addressed.

United Kingdom patent 1,397,102 is directed to the problem of cross contamination introduced onto a smooth surface when it is cleaned with an abrasive cleaner to prepare the surface for receiving a coating.

The patent suggests using dry ice particles as shot to bombard the surface being prepared to receive a coating. The dry ice subsequently vaporizes leaving behind no cross contamination residue. West German patent application DE 37 20 992A1 likewise relates to a method for cleaning blast tool surfaces using dry ice particles. However, neither of these references address the cross contamination and biocompatibility problems associated with cleaning porous coated or roughened surface implants to avoid debris effects within the human body.

There yet exists a need for a process to clean medical implants supplied with a porous coating. The method should not damage the porous coating but should remove substantially all debris from the surface as well as any loosely-held particulates of the coating so that these will not separate from the implant in the recipient's body at a later time causing undesirable medical effects. Further, the method should not introduce cross contaminating debris into the implant surface but should provide a cleaned implant surface containing a reduced number and size of loose or potentially loose debris particles. Finally, the cleaning method should desirably provide a surface that is readily amenable for further treatment, such as passivation, and implantation into a recipient.

SUMMARY OF THE INVENTION

The invention provides a method for the cleaning of roughened surface or porous-coated medical implants of all kinds, including orthopedic, cardiovascular, dental, neurological, percutaneous, and the like.

In the invention cleaning, a roughened surface or porous-coated medical implant is subjected to blasting with selected particulate solids. These particulate solids are selected from the solids that deliquesce, sublimate or vaporize but that are sufficiently hard to provide an effective impact for dislodging debris and loosely attached particulates from the implant surface. Further, the selected solid particulates also include those soluble solids that are non-toxic and readily dissolved in a biocompatible, non-toxic solvent that is not harmful or adversely reactive with the medical implant or porous coating material.

After blasting with the particulate solids, the porous-coated implant may optionally be subjected to ultrasonic treatment to further clean the surface. In general, solutions in the ultrasonic treatment are selected based upon the solids used in the particulate solid blasting step. Thus, when a hard soluble solid is used as the particulate in the blasting stage, then a solvent for that solid may be used in the ultrasonic treatment step. When the solid used for blasting is one which can deliquesce, sublimate or vaporize, the ultrasonic treatment may not be necessary.

As an alternative to ultrasonic treatment, or in addition to such treatment, when soluble blasting particle fragments are lodged in/on the porous coating or roughened surface of the implant, these may be dissolved in a biocompatible solvent by immersing the implant's surface in the solvent or running solvent over the surface.

The invention cleaning method is applicable, in particular, to metallic or ceramic porous coatings on implants. However, the method may also be used when the porous coating is of an organic polymeric nature. Depending upon the nature of the coating hardness, fineness of pore, fragility of coating particles, and the like, blasting parameters may readily be adjusted to obtain the desired cleaning effect without damage to the integrity of the porous coating. Thus, judicious selection of operating variables such as the hard particle used for shot blasting, the blasting pressure and blasting nozzle distance from the porous surface, will provide good cleaning.

While the invention method is especially useful for cleaning porous coatings where it has marked advantages over other methods, it is clearly also useful to clean smooth surfaces or other types of coatings on medical implants. Further, while the method is applicable to metallic implants with porous metallic or ceramic coatings, it is also contemplated as useful for non-metallic (polymeric or ceramic) implants with porous coatings or roughened surfaces.

After treatment by the invention blasting and optional ultrasonic treatment process, a porous coating or toughened surface of a medical implant will contain a reduced number and size of residual debris or potentially loose debris particulates. Consequently, the biocompatibility of the implant is enhanced and the risk of adverse side effects to a recipient due to the release of debris is significantly reduced. Further, the treated medical implant's surface may then be readily further treated, such as by passivation, to produce an implant suitable for implantation into a recipient.

DETAILED DESCRIPTION OF THE PREFERRED EMBODIMENTS

Figure 1:
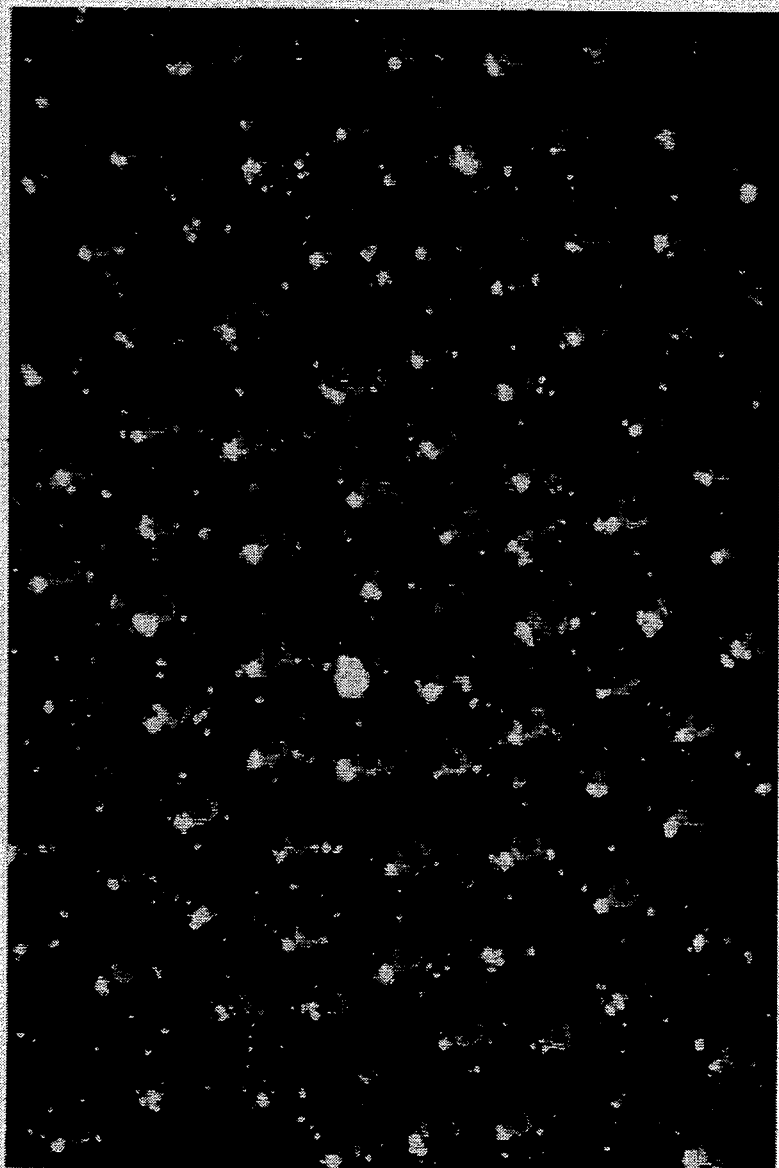
FIG. 1 is an optical photomicrograph of a porous coating shown as sintered cobalt-chrome-molybdenum beads on a cobalt-chrome-molybdenum substrate.

The invention provides methods of cleaning medical implants having surfaces at least partially covered with a porous coating. These porous coatings may be created by any of the methods conventionally used, such as attaching a layer of beads to the surface by sintering, diffusion bonding wire mesh to the surface, or plasma-spraying metallic powders, and the like onto an implant's surface. Such porous coatings or roughened surfaces are intended to either promote bone or tissue ingrowth or ongrowth into surface pores thereby enhancing the fixation of the medical implant in a recipient's body. The reference to "porous coated surface" in the specification and claims should therefore be understood to encompass all the non-smooth surfaces that are applied to medical implants to promote either bone tissue ingrowth to enhance fixation of the implant in a recipient's body, or that promote soft tissue ingrowth and coating over the implant surface so that the implant presents a more biocompatible "living tissue" surface to other body tissue, for instance so that it is more compatible with blood or improves the anchoring of dental implants, in the recipient's body. This includes coatings produced by adhering beads, wire mesh and the like to the implant's surface. The reference to "roughened" surfaces includes surfaces that have been toughened by shot blasting, machining or other processes to produce a rough surface that by reason its process of manufacture contains loosely-adhered surface particles that may detach in the body after implantation to induce debris-related health problems.

In the invention method, the porous coated or roughened surfaces of medical implants are subjected to impact by particulate solids that either readily vaporize or liquify or that are readily soluble in solutions that are not toxic and not harmful to the surface of the medical implant. The particulate solids that vaporize include, for example, frozen carbon dioxide (dry ice), and the like. The particulate solids that liquify include, for example, ice, frozen saline solution, other frozen salt solutions, and the like. The solids that are soluble in a nontoxic solvent that is not harmful to the medical implant include alkaline metal chlorides, sulfates, nitrates, sulfites, nitrites, bisulfites, and the like, of sodium, calcium, potassium, magnesium, phosphorous and the like; other metal salts, salt containing non-aggressive oxyanions, and the like.

The useful particulate solids should be projected at the surface of the implant at such a velocity that the resultant impact is sufficiently large to dislodge particles of debris held in the interstices of the porous coating and also should be sufficiently large and hard to dislodge and remove any loosely adherent sections of the coating. Since the density of the useful particulate solids encompasses a wide range, sufficient impact may be generated by either enlarging the size (and hence mass) of the particle or increasing the speed at which it impacts the porous coated or roughened surface. Desirably, the particulate size and hardness should be selected to enhance cleaning and should therefore bear a relation to the size or structure of pores on the porous coated surface. Particle size therefore ranges from about 10 to about 2,000 micron diameter, preferably from about 50 to about 1,500 micron diameter. These size ranges are selected to allow impact on and into interstitial spaces of the porous coated surface while the velocity and hardness of the particulate solids may be adjusted to ensure sufficiently high impact to remove debris held in the interstitial spaces and also removal of loosely adherent particles of porous coatings and roughened surfaces.

FIG. 1 is an optical micrograph of cobalt-chrome-molybdenum beads sintered onto an underlying substrate, magnified 15 times. The photograph clearly shows beads, some of them welded together, and interstitial spaces between these beads wherein debris may lodge during the manufacturing process. Such debris is not readily dislodged with conventional cleaning methods. Further, the use of silicon carbide, alumina, silica, and other hard particles for cleaning porous surfaces results in cross-contamination in that fragments of these hard particles lodge into the surface or within the interstitial spaces. Upon implantation of the medical implant into a recipient, these fragments leach out and contaminate body tissue potentially leading to adverse tissue reaction.

After the porous coated surface has been impact cleaned with particulate solids, as described above, it may optionally be further cleaned by ultrasonic cleaning. As is conventional in this type of treatment, the porous coated implant is placed in a liquid and subjected to ultrasonic frequency vibration to remove any residual debris, loosened particulates of the porous coating and any residual impact particulates from the surface of the porous coating. The liquid may be selected from any of the non-toxic liquids that do not adversely affect the surface of the medical implant. In particular, when the hard particulate used in impact cleaning is not of the type that vaporizes or liquifies, then the liquid used for ultrasonic cleaning should be a solvent for the hard particulate so that any hard particulate fragments held in interstitial spaces on the porous coating will be dissolved and removed from the porous coating. The useful liquids include water, metal salt solutions, alcohol, mild acids or bases, and the like. Typically, the ultrasonic treatment is carried out for from about 1 to about 60 minutes, preferably from about 5 to about 30 minutes, to effectively remove residual debris, loosened particulates of the roughened or porous coating, and any residual particulate used in the blasting process.

As an alternative, the roughened surface or porous coated implant surface may be washed by a solvent for the soluble hard particle used in the blast-cleaning step. This washing may be by immersion or rinsing with preferably a biocompatible solvent.

After ultrasonically cleaning or rinsing or immersing, the porous coated or roughened surface, the surface may then be treated according to other conventional methods before being implanted into a recipient. These conventional methods include dipping in nitric acid to passivate the surface or immersing in a solution of non-aggressive oxyanions, as is disclosed in our U.S. Pat. No. 5,211,663, filed Jun. 24, 1992, hereby fully incorporated by reference. In the non-aggressive oxyanion passivation methods, the metallic implant surfaces are either spontaneously or galvanically passivated in aqueous water soluble salt solutions, preferably alkaline metal salt solutions, containing non-aggressive oxyanions such as sulfate, phosphate, di-hydrogen phosphate, mono-hydrogen phosphate, borate, and the like. Galvanic passivation in these electrolytic solutions may be achieved by galvanic coupling of the metal or alloy implant with an electrochemically more noble material, such as carbon. Such passivation methods, utilizing non-aggressive oxyanions, provide a thin and uniform passivated surface on the metal implant, thereby rendering the implant more electrochemically stable in the biological environment, and therefore more biocompatible. Additionally, since the nature of the passivating solutions is more similar to that of body fluids, than nitric acid, the protective ability of the passive film, when exposed to the body fluids, undergoes much less alteration. This method also reduces the disadvantageous effects of initial surface conditions on the effectiveness of passivation largely because of the absence of aggressive species that may further enhance the non-uniform character of the initial surface film. In the galvanic method there is galvanic coupling of the metal or alloy implant with, for instance, carbon. Without being bound, it is theorized that the macroscopic separation of anodic and cathodic processes may give rise to a lower local pH at the metal surface and this may assist in the removal of undesirable corrosion products from the passive film. Since the breakdown potential in the passivating solution is much more positive than the potential at which anodic dissolution takes place, no specific restriction on the metal/carbon surface area ratio is necessary.

EXAMPLES

The examples that follow serve as illustrations only and do not limit the scope of the invention as described above and claimed herebelow.

EXAMPLE 1

A 1" diameter Ti-6A1--4V coupon was coated with a porous coating of titanium powder to a coating thickness of approximately 0.02 inches (500 microns). Sodium chloride crystals (stock grade Morton TM salt) were blasted onto the porous coating at 90 psi for about one minute from a working distance of 3 inches using a blasting apparatus sold by Econoline Manufacturing, Inc. of Grand Haven, Michigan.

The salt-blasted coupon was subsequently cleaned ultrasonically in water for 15 minutes to remove loosened debris and coating particulates and to ensure that any residual salt was dissolved. The pull-off strength of the porous coating was then determined by applying a film of FM 1000 epoxy adhesive film (sold by American Cyanamid) to the coating, and placing a cylindrical threaded test piece lengthwise on top of the epoxy film. The assembled sandwich of coupon, film and test piece was then cured in a oven for 2 hours at 177° C. to allow adhesion of the epoxy to both the test piece and the porous-coated surface of the coupon. The assembly was then placed in a test apparatus and the pull-off strength of the coating was measured by exerting force on the threaded cylindrical piece until it separated from the coupon. In this case, separation was achieved by failure at the coupon-porous coating interface and therefore measured the strength of adherence of the porous coating to the substrate. This was approximately 4,100 psi. By comparison, when the pull off strength of the coating of a similarly coated coupon, which did not undergo the invention cleaning treatment, was measured, it was found to be 4,480±350 psi. Thus, the invention porous coating cleaning process does not appear to adversely affect the pull off strength of the porous coatings.

EXAMPLE 2

Four coupons of 1" diameter titanium with a porous titanium coating were tested as controls for coating strength adherence. The coating thickness on these substrates were also approximately 0.02 inches (500 microns).

Two other, identical coupons were cleaned, using the cleaning procedure described in Example 1, to remove surface debris, loosely-held coating particulates, and any residual salt from their coatings. The pull-off strengths of these two porous coated coupons were determined as described in Example after the cleaning treatment. These pull-off strengths are shown in Table I.

TABLE I

Pull-Off Strength of Porous Coatings
With and Without the Invention Cleaning Treatment

| Specimen | Pull-Off Strength Before Cleaning (psi) | Pull-Off Strength After Cleaning (psi) | Failure Mode |
| --- | --- | --- | --- |
| 1 | 5,817 | — | Coupon-coating interface |
| 2 | 3,531 | — | Epoxy failure |
| 3 | 5,252 | — | Epoxy failure |
| 4 | 3,332 | — | Epoxy failure |
| 5 | — | 8,560 | Coupon-coating interface |
| 6 | — | 8,266 | Coupon-coating interface |

Based upon the above results, the cleaning process does not adversely affect adherence of the coating to the coupons.

EXAMPLE 3

Samples of titanium alloy substrate were coated with commercially pure titanium to provide a porous coating of thickness of approximately 0.02 inches (500 microns). These specimens were blasted with USP grade sodium chloride crystals (Morton TM salt) at 60 psi for 30 seconds at a distance of 3 inches using a benchtop blast cabinet model SCC2218 manufactured by Scott Chemical and Cleaning of Memphis, Tennessee. The specimens were subsequently cleaned ultrasonically in water for 30 minutes to remove any loosened debris and coating particulates and to ensure that any residual salt was dissolved.

After this cleaning treatment, three of the specimens (total porous coating surface area=2.36 sq. in.) were subjected to ultrasonic vibration together in deionized water for one hour to further remove any loose debris from the specimens. Debris collected in the deionized water was quantified using a Spectrex SPC-510 laser particle counter. The water sample was tested four times to obtain readings 1–4 shown in Table II. This debris was compared with debris generated by three control specimens which were not subjected to the invention cleaning treatment but were only subjected to one hour of ultrasonic vibration to obtain debris samples. The results obtained are compared in Table II below.

TABLE II

| Test No. | Controls | After Invention Process |
| --- | --- | --- |
| | Number of Particles $\times 10^6$ | |
| 1 | 19.9 | 4.86 |
| 2 | 21.57 | 5.63 |
| 3 | 13.50 | 2.78 |
| 4 | 17.89 | 2.48 |
| | Average Particle Sizes ($\mu$) | |
| 1 | 1.87 | 1.32 |
| 2 | 1.91 | 1.34 |
| 3 | 2.00 | 1.36 |
| 4 | 2.17 | 1.19 |

From the results, both the number and size of particles produced by ultrasonic vibration is significantly reduced when the samples have undergone the invention cleaning process.

Although the invention has been described with reference to its preferred embodiments, those of ordinary skill in the art may, upon reading this disclosure, appreciate changes and modifications which do not depart from the scope and spirit of the invention as described above or claimed hereafter.

We claim:

1. A method of cleaning a medical implant having a porous-coated or roughened surface, the surface containing loose debris particles and loosely-adherent debris particles, the method comprising:

(a) impacting the porous-coated or roughened surface with particles of soluble solids selected from alkaline metal salts having anions selected from the group consisting of sulfate, phosphate, di-hydrogen phosphate, mono-hydrogen phosphate, borate, nitrate, nitrite, chloride, sulfite, and bisulfite, said soluble solids be of sufficient hardness and density to effectively dislodge and remove debris from the surface said particles propelled by a carrier fluid; and (b) subjecting the impacted surface to ultrasonic cleaning in the presence of a solvent for the soluble solid to dissolve residual soluble solids left behind on the impacted surface and remove debris particles;

whereby the number and size of residual debris particles on the implant surface is reduced.

2. The method of claim 1, further comprising passivating the impacted, treated implant surface by immersing the surface in a solution containing anions selected from the group consisting of sulfate, phosphate, di-hydrogen phosphate, mono-hydrogen phosphate and borate.

3. The method of claim 1, further comprising passivating surfaces of the medical implant by immersing in a passivating acid solution.

4. A method of cleaning a medical implant having a porous-coated or roughened surface, the surface containing loose debris particles and loosely-adherent debris particles, the method comprising:
(a) impacting the porous-coated or toughened surface with particles propelled by a carrier fluid, said particles selected from the group consisting of frozen gases and frozen liquids to remove debris and loosely-adherent coating particles from the surfaces, whereby the number and size of residual debris particles and loosely-adherent coating particles on the roughened or porous-coated surface is reduced;
(b) optionally, treating the impacted surface with a liquid solvent for further removal of debris from the surface; and
(c) passivating impacted surfaces of the medical implant by immersing the surfaces in a passivating solution.

5. The method of claim 4, wherein the treating comprises:
subjecting the impacted surface to ultrasonic treatment in a liquid medium to remove residual loosely-adherent debris from the surface.

6. The method of claim 4, wherein the treating comprises:
rinsing the impacted surface in a stream of biocompatible solvent to wash residual loosely-adherent debris from the surface.

7. The method of claim 4, wherein the passivating comprises:
immersing surfaces of the medical implant in a solution of non-aggressive oxyanions.

8. The method of claim 4, wherein the passivating comprises:
immersing surfaces of the medical implant in a passivating acid solution.

9. A method of cleaning a medical implant having a roughened or porous-coated surface, the surface containing loose debris and loosely-adherent debris particles, the method comprising:
impacting the porous-coated or toughened surface with particles propelled by a carrier fluid, said particles selected from the group consisting of solids that sublimate, solids that dissolve and solids that deliquesce, said particles having sufficient density and hardness to effectively dislodge and remove debris from the surface, whereby the number and size of residual debris particles on the implant surface is reduced; and
passivating impacted surfaces of the medical implant with a passivating solution.

10. The method of claim 9, further comprising rinsing the impacted surfaces with a non-toxic solvent to remove loosely-adherent and loose debris.

11. The method of claim 9, wherein the particles of solid are selected from the group consisting of frozen carbon dioxide, frozen salt solutions and ice.

12. The method of claim 9, wherein the:
passivating comprises immersing the impacted surfaces in a solution containing anions selected from the group consisting of sulfate, phosphate, dihydrogen phosphate, monohydrogen phosphate and borate.

13. The method of claim 9, wherein the passivating comprises immersing surfaces of the medical implant in a passivating acid solution.

14. The method of claim 9, further comprising subjecting the impacted surfaces to ultrasonic treatment.

15. The method of claim 9, further comprising rinsing the impacted surface with a biocompatible solvent to remove debris from the surface.

* * * * *